(12) United States Patent
Kanda

(10) Patent No.: US 7,773,801 B2
(45) Date of Patent: Aug. 10, 2010

(54) LEARNING-TYPE CLASSIFYING APPARATUS AND LEARNING-TYPE CLASSIFYING METHOD

(75) Inventor: Yamato Kanda, Hino (JP)

(73) Assignee: Olympus Corporation, Tokyo (JP)

( * ) Notice: Subject to any disclaimer, the term of this patent is extended or adjusted under 35 U.S.C. 154(b) by 972 days.

(21) Appl. No.: 11/520,555

(22) Filed: Sep. 13, 2006

(65) Prior Publication Data

US 2007/0009152 A1 Jan. 11, 2007

Related U.S. Application Data

(63) Continuation of application No. PCT/JP2005/006170, filed on Mar. 30, 2005.

(30) Foreign Application Priority Data

Mar. 31, 2004 (JP) .............................. 2004-107738

(51) Int. Cl.
G06K 9/62 (2006.01)
(52) U.S. Cl. ....................... 382/159; 382/224
(58) Field of Classification Search ................. 382/159, 382/224–225, 309, 149; 700/47, 48
See application file for complete search history.

(56) References Cited

U.S. PATENT DOCUMENTS

| | | | |
|---|---|---|---|
| 6,546,308 B2 * | 4/2003 | Takagi et al. ................. | 700/121 |
| 2001/0011706 A1 | 8/2001 | Nara et al. | |
| 2002/0001404 A1 | 1/2002 | Yoshikawa et al. | |

FOREIGN PATENT DOCUMENTS

| | | | |
|---|---|---|---|
| JP | 8-021803 A | 1/1996 | |
| JP | 11-344450 A | 12/1999 | |
| JP | 2000-57349 A | 2/2000 | |

OTHER PUBLICATIONS

Supplementary European Search Report dated Apr. 24, 2009 (3 pages), issued in counterpart European Application Serial No. 05721668.1.
Notification Concerning Transmittal of International Preliminary Report on Patentability, Chapter 1 of the Patent Cooperation Treaty, and Written Opinion of the International Searching Authority, dated Oct. 26, 2006,for PCT/JP2005/006170, 5 sheets.

* cited by examiner

*Primary Examiner*—Daniel G Mariam
(74) *Attorney, Agent, or Firm*—Frishauf, Holtz, Goodman & Chick, P.C.

(57) ABSTRACT

A learning-type classifying apparatus comprises defective region extracting unit for extracting defective regions of classification targets from an image in which the plurality of regions of the classification targets are present, characteristic value calculating unit for calculating characteristic values for the extracted regions of the classification targets, classifying unit for classifying the extracted regions of the classification targets into predetermined classes on the basis of the calculated characteristic values, region integrating unit for integrating the regions which belong to the same class as a result of the classification, display unit for displaying images of the integrated regions and the classification results, input unit for correcting errors in the classification results, and teacher data creating unit for creating teacher data for each of the regions so that the classification results of the integrated regions are reflected in each region included in the integrated regions.

16 Claims, 8 Drawing Sheets

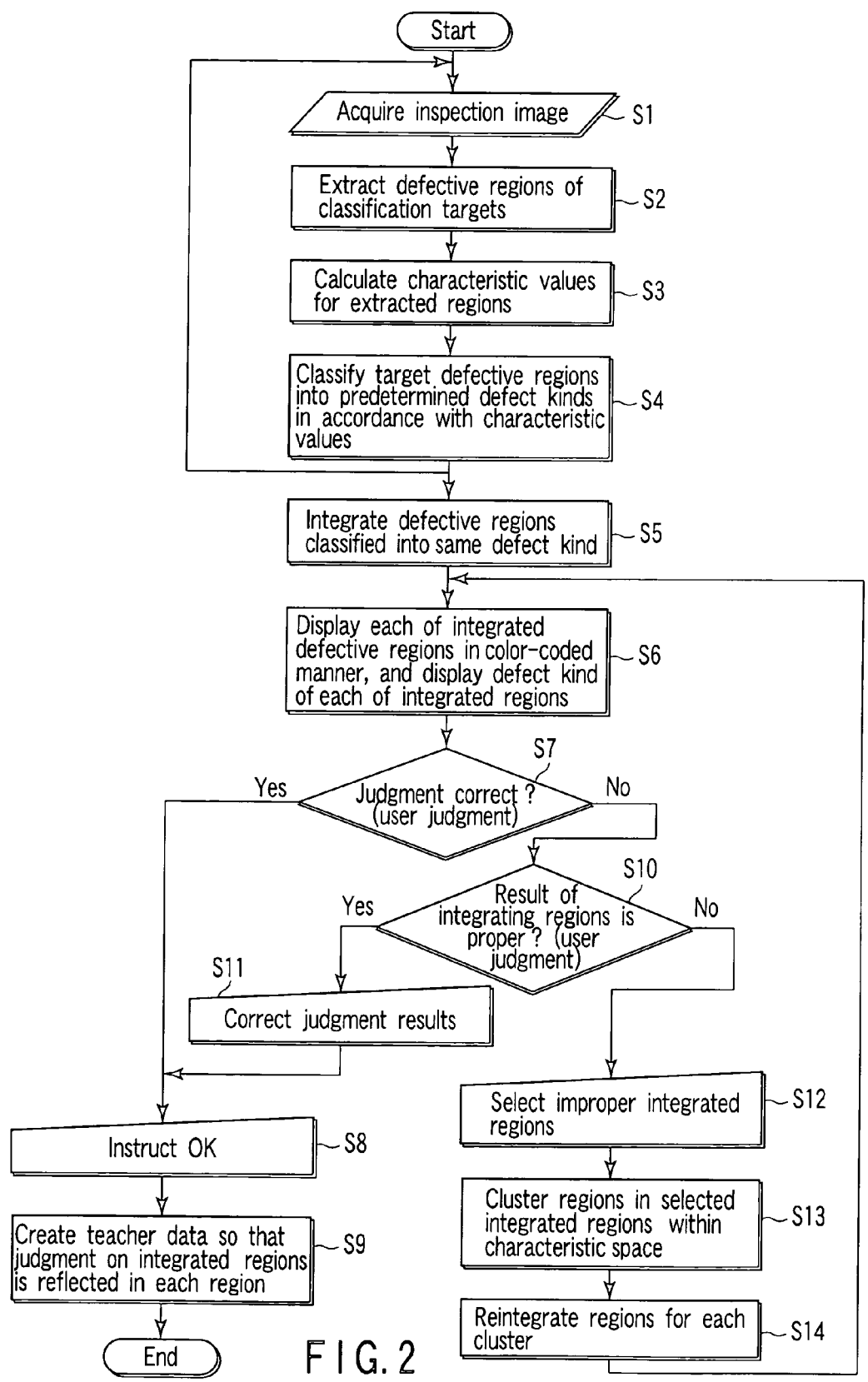
F I G. 2

| Teacher data | | | | | | |
|---|---|---|---|---|---|---|
| | Characteristic value 1 | Characteristic value 2 | Characteristic value 3 | Characteristic value 4 | Characteristic value 5 | Judgment |
| Region 151 | 0.44 | 0.36 | 0.66 | 0.24 | 0.11 | Defect A |
| Region 152 | ... | ... | ... | ... | ... | Defect A |
| Region 153 | ... | ... | ... | ... | ... | Defect A |
| Region 154 | ... | ... | ... | ... | ... | Defect A |
| Region 155 | ... | ... | ... | ... | ... | Defect B |
| Region 156 | ... | ... | ... | ... | ... | Defect B |
| Region 157 | ... | ... | ... | ... | ... | Defect C |
| Region 158 | ... | ... | ... | ... | ... | Defect A |
| Region 159 | ... | ... | ... | ... | ... | Defect A |

| Teacher data | | | | | | |
|---|---|---|---|---|---|---|
| | Characteristic value 1 | Characteristic value 2 | Characteristic value 3 | Characteristic value 4 | Characteristic value 5 | Judgment |
| Region 151 | 0.44 | 0.36 | 0.66 | 0.24 | 0.11 | Defect A |
| Region 152 | ... | ... | ... | ... | ... | Defect A |
| Region 153 | ... | ... | ... | ... | ... | Defect A |
| Region 154 | ... | ... | ... | ... | ... | Defect E |
| Region 155 | ... | ... | ... | ... | ... | Defect B |
| Region 156 | ... | ... | ... | ... | ... | Defect B |
| Region 157 | ... | ... | ... | ... | ... | Defect C |
| Region 158 | ... | ... | ... | ... | ... | Defect D |
| Region 159 | ... | ... | ... | ... | ... | Defect E |

LEARNING-TYPE CLASSIFYING APPARATUS AND LEARNING-TYPE CLASSIFYING METHOD

CROSS REFERENCE TO RELATED APPLICATIONS

This is a Continuation Application of PCT Application No. PCT/JP2005/006170, filed Mar. 30, 2005, which was published under PCT Article 21(2) in Japanese.

This application is based upon and claims the benefit of priority from prior Japanese Patent Application No. 2004-107738, filed Mar. 31, 2004, the entire contents of which are incorporated herein by reference.

BACKGROUND OF THE INVENTION

1. Field of the Invention

The present invention relates to a learning-type classifying apparatus and a learning-type classifying method.

2. Description of the Related Art

As a learning-type classifying apparatus, the configuration of an apparatus is shown in Jpn. Pat. Appln. KOKAI Publication No. 8-21803 wherein a neural network is so constructed that characteristic values of the defective portion extracted from within an image is input as an input pattern, and the kind of defect is output by learning, thereby classifying the defect.

Furthermore, Jpn. Pat. Appln. KOKAI Publication No. 11-344450 shows a configuration which assists a teacher data creating operation, a configuration which uses statistical discrimination analysis to classify defective images on the basis of the created teacher data, etc. It is to be noted that the teacher data is a set of characteristic value information calculated from image information on or an image of a classification target and information on a correct class (=correct category) of the target (see FIG. 4 in the above-mentioned publication).

BRIEF SUMMARY OF THE INVENTION

According to a first aspect of the present invention, there is provided a learning-type classifying apparatus comprising: region extracting unit for extracting regions of classification targets from an image in which the plurality of regions of the classification targets are present; characteristic value calculating unit for calculating characteristic values for the extracted regions of the classification targets; classifying unit for classifying the extracted regions of the classification targets into predetermined classes on the basis of the calculated characteristic values; region integrating unit for integrating the regions which belong to the same class as a result of the classification; display unit for displaying images of the integrated regions and the classification results; input unit for correcting errors in the classification results; and teacher data creating unit for creating teacher data for each of the regions so that the classification results of the integrated regions are reflected in each region included in the integrated regions.

According to a second aspect of the present invention, there is provided a learning-type classifying apparatus according to the first aspect, wherein when erroneously integrated regions are selected by the input unit, the region integrating unit divides a plurality of regions in the integrated regions into at least two or more clusters within a characteristic space, and reintegrates the regions belonging to each cluster one by one.

According to a third aspect of the present invention, there is provided a learning-type classifying apparatus according to the second aspect, wherein the clusters are created by use of a distance on a characteristic axis specified by the input unit.

According to a fourth aspect of the present invention, there is provided a learning-type classifying apparatus according to the first aspect, further comprising judging unit for judging the necessity of creating additional teacher data from changes in the percentage of classification correctness in each class along with an increase in the number of teacher data.

According to a fifth aspect of the present invention, there is provided a learning-type classifying apparatus according to the second aspect, further comprising judging unit for judging the necessity of creating additional teacher data from changes in the percentage of classification correctness in each class along with an increase in the number of teacher data.

According to a sixth aspect of the present invention, there is provided a learning-type classifying apparatus according to the third aspect, further comprising judging unit for judging the necessity of creating additional teacher data from changes in the percentage of classification correctness in each class along with an increase in the number of teacher data.

According to a seventh aspect of the present invention, there is provided a learning-type classifying method comprising: extracting regions of classification targets from an image in which the plurality of regions of the classification targets are present; calculating characteristic values for the extracted region; classifying the regions into predetermined classes on the basis of the calculated characteristic values; integrating the regions which belong to the same class as a result of the classification; displaying images of the integrated regions and the classification results; acquiring instruction information to correct errors in the classification results; and creating teacher data for each of the regions so that the classification results of the integrated regions are reflected in each region included in the integrated regions.

According to an eighth aspect of the present invention, there is provided a learning-type classifying method according to the seventh aspect, wherein when erroneously integrated regions are selected by the acquired instruction information, a plurality of regions in the integrated regions are divided into at least two or more clusters within a characteristic space, and the regions belonging to each cluster are reintegrated one by one.

According to a ninth aspect of the present invention, there is provided a learning-type classifying method according to the seventh aspect, wherein the clusters are created by use of a distance on a characteristic axis specified by the input unit.

According to a tenth aspect of the present invention, there is provided a learning-type classifying method according to the seventh aspect, wherein the necessity of creating additional teacher data is judged from changes in the percentage of classification correctness in each class along with an increase in the number of teacher data.

BRIEF DESCRIPTION OF THE SEVERAL VIEWS OF THE DRAWING

FIG. 2 is a flowchart for explaining the flow of processing in the defect classifying apparatus of the first embodiment;

DETAILED DESCRIPTION OF THE INVENTION

Embodiments of the present invention will hereinafter be described in detail with reference to the drawings. Here, a defect classifying apparatus for semiconductor macro-inspection (refer to Jpn. Pat. Appln. No. 2001-370218 for description of the semiconductor macro-inspection) will be described by way of example as the embodiments of the present invention. However, the learning-type classifying apparatus of the present invention is also applicable to other classifying apparatuses in a case where a plurality of kinds of classification targets (e.g., cells) are present in an inspection image.

First Embodiment

Figure 1:
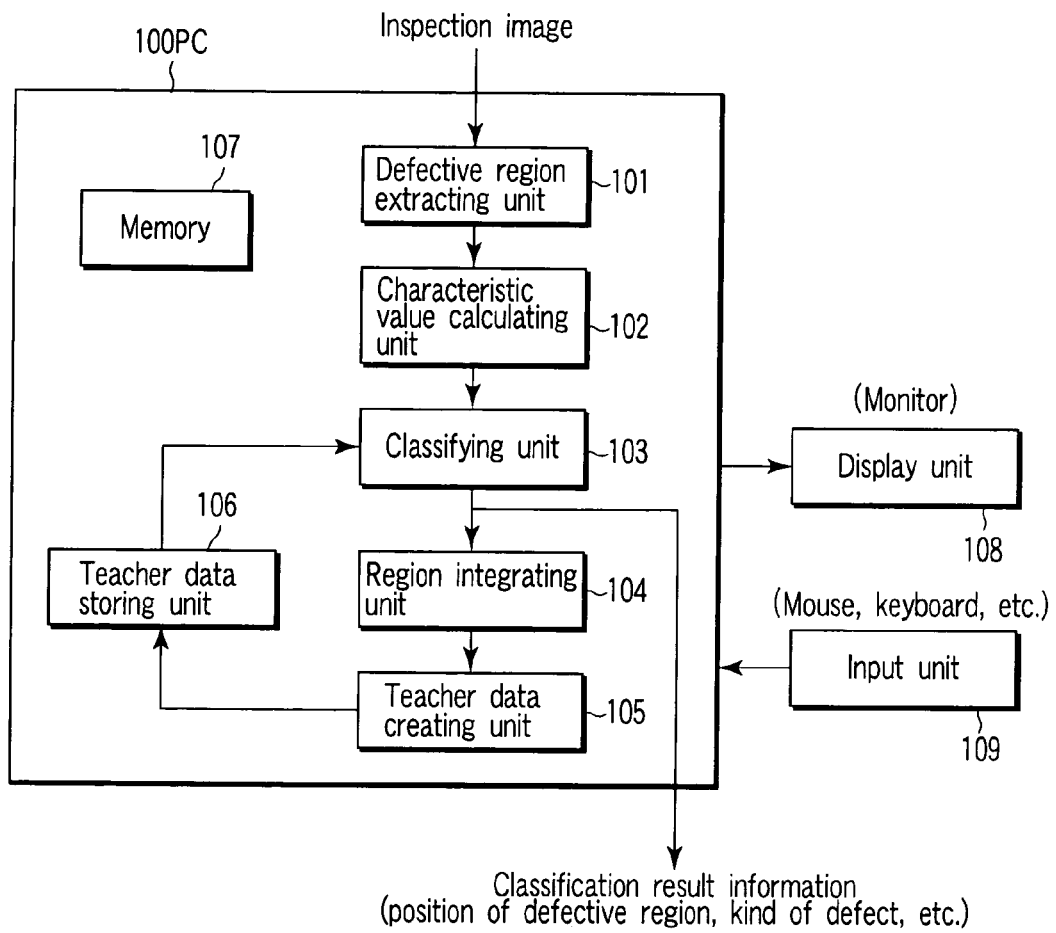
FIG. 1 is a diagram showing the configuration of a defect classifying apparatus according to a first embodiment of the present invention.

FIG. 1 is a diagram showing the configuration of a defect classifying apparatus according to a first embodiment of the present invention, and the apparatus comprises: defective region extracting unit 101, characteristic value calculating unit 102, classifying unit 103, region integrating unit 104, teacher data creating unit 105, teacher data storing unit 106, a memory 107, display unit 108 and input unit 109. Here, the defective region extracting unit 101, the characteristic value calculating unit 102, the classifying unit 103, the region integrating unit 104 and the teacher data creating unit 105 are embodied by a CPU in a PC 100. The teacher data storing unit 106 is embodied by a hard disk in the PC 100. The memory 107 is embodied by a memory in the PC 100. In addition, the display unit 108 is embodied by a monitor, and the input unit 109 is embodied by a mouse, keyboard, etc.

It is to be noted that a configuration for acquiring an inspection image is not specifically limited and is therefore not shown. However, for example, it is achieved by imaging a specimen by a CCD camera and loading the image into the memory in the PC 100 through an image input board. In addition, a configuration associated with the processing of classification result information is not specifically limited either and is therefore not shown.

FIG. 2 is a flowchart for explaining the flow of processing in the defect classifying apparatus described above. The processing in the present defect classifying apparatus includes two flows for processing during learning (during the creation of teacher data) and processing during inspection. In FIG. 2, the processing during learning (during the creation of the teacher data) is achieved by steps S1 to S4, while the processing during inspection is achieved by repeating steps S1 to S4.

The flow of processing shown in FIG. 2 will be described below referring to FIG. 1. First, the defect classifying apparatus acquires an inspection image including defective portions of classification targets (step S1). Next, in the defective region extracting unit 101, the defective regions of the classification targets are extracted from the acquired inspection image (step S2). For the extraction of the defective regions in step S2, there are a method in which a referential nondefective image of the inspection target is previously retained and this image is compared with the inspection image to extract regions having abnormal luminance as defective regions, and a method in which the periodicity of regularly arranged patterns is used and small sections having the same pattern are compared with each other to extract regions having abnormal luminance as defective regions. Moreover, when the defective portions are imaged with luminance different from that of portions therearound, there is a method of extracting by digital processing without requiring a comparative target.

After the defective regions are extracted, a characteristic value of each of the defective regions is calculated in the characteristic value calculating unit 102 (step S3). It is to be noted that the same defect may be extracted in a divided state during the extraction of the regions due to effects of a foundation pattern, dicing lines and the like in, for example, a semiconductor wafer. For this reason, the characteristic values are calculated after the regions are coupled by, for example, morphology processing ([reference] Corona Corporation: Morphology written by Hidefumi Kobatake) as required. The characteristic value here concerns the size, shape, position, concentration and texture of a single extracted region, or an arrangement structure formed by a plurality of regions, or the like. The characteristic value in a macro-inspection is disclosed in Jpn. Pat. Appln. No. 2003-168114 by the present inventor.

It is to be noted that the method of extracting regions and the method of calculating the characteristic values are modified in accordance with the targets for classification, and do not limit the contents of the present invention.

After the characteristic values of the regions are calculated, the defective regions are classified into predetermined defect kinds in the classifying unit 103 (step S4). As a method of classification, there is a method (k neighborhood method) comprising prestoring several teacher data in the teacher data storing unit 106, selecting, from these teacher data, k teacher data located in the neighborhood of the defective regions of the classification targets within a characteristic space, and classifying them into a defect kind having the largest number. It is to be noted that when there is no previous teacher data at the initial stage of learning, defective regions in a screen are properly classified and assigned with temporary defective kinds (information on a correct defect kind is obtained by the subsequent user operation) in accordance with a method similar to clustering processing described later.

During an inspection, information on classification results obtained in step S4 is output, and, for example, this information is used as input information for subsequent processing such as measurement processing and recovery processing corresponding to the classification results, or is recorded to, for example, check the results in large units.

On the other hand, the following processing is performed during learning (during the creation of teacher data) after the above processing in step S4. First, the defective regions classified into the same defect kind in the classifying unit 103 are integrated in the region integrating unit 104 (step S5). After the integration of the defective regions, each of the integrated regions is displayed in an identifiable manner (e.g., in a color-coded manner) and the defect kinds of the integrated regions are displayed on the display unit 108 (step S6).

Figures 3, 4:
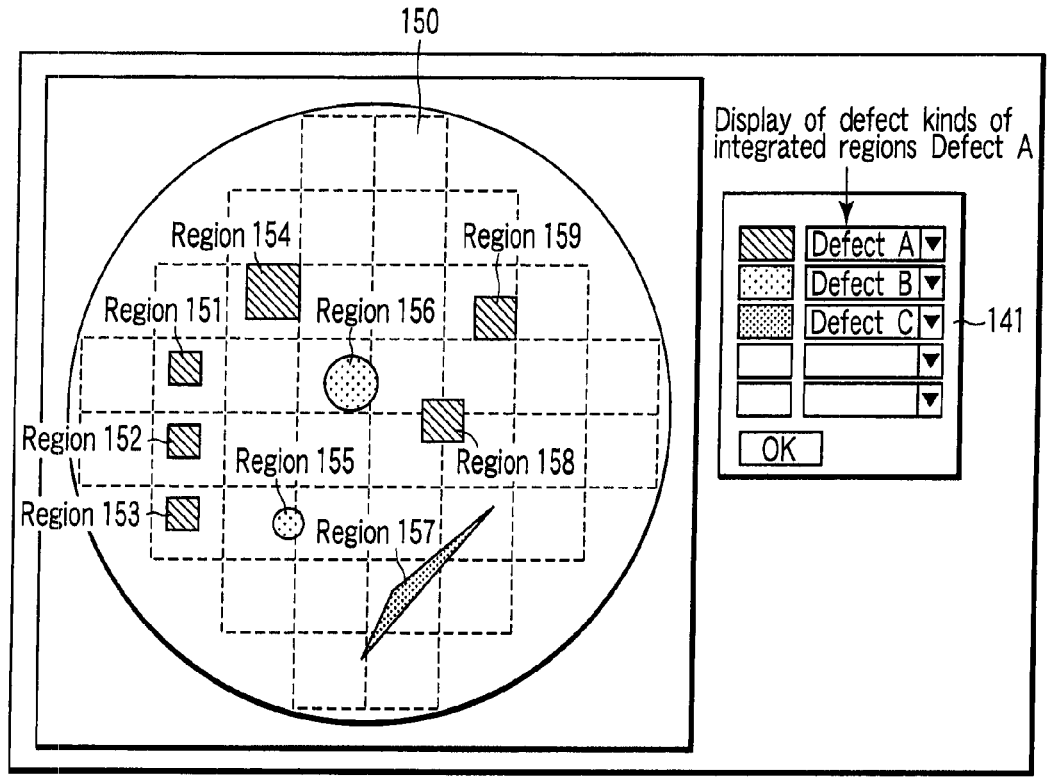
FIG. 3 is a diagram showing one example of a display screen on display unit 108 when step S6 is executed.
FIG. 4 is a diagram showing teacher data created on the basis of the display state shown in FIG. 3.

FIG. 3 shows one example of a display screen on the display unit 108 when step S6 is executed. The screen has a display area 150 for displaying each of the integrated regions in a color-coded manner, and a display area 141 for displaying the defect kinds of the integrated regions. Here, displays of the same color are expressed with the same kind of design. Therefore, among regions 151 to 159 displayed in the display area 150 in FIG. 3, the regions 151 to 154, 158 and 159 are displayed in an integrated manner in the same color as regions belonging to the same defect kind, the regions 155 and 156 are displayed in an integrated manner in another same color as regions belonging to another same defect kind, and the region 157 is displayed in still another color as a region belonging to still another same defect kind. Moreover, the display area 141 indicates that the defect kind of the regions 151 to 154, 158 and 159 belongs to a defect A, the defect kind of the regions 155 and 156 belongs to a defect B, and the defect kind of the region 157 belongs to a defect C.

Here, a user determines whether a judgment on the display results on the display screen is correct or wrong (step S7). When the judgment is correct, the user instructs using the input unit 109 that the judgment results are OK (step S8). After the OK instruction in step S8, the classification results of the integrated regions are considered as the classification results of the respective regions included in each of the integrated regions, thereby creating the teacher data in the teacher data creating unit 105 (step S9). FIG. 4 shows the teacher data created on the basis of the display state shown in FIG. 3.

Figure 5:
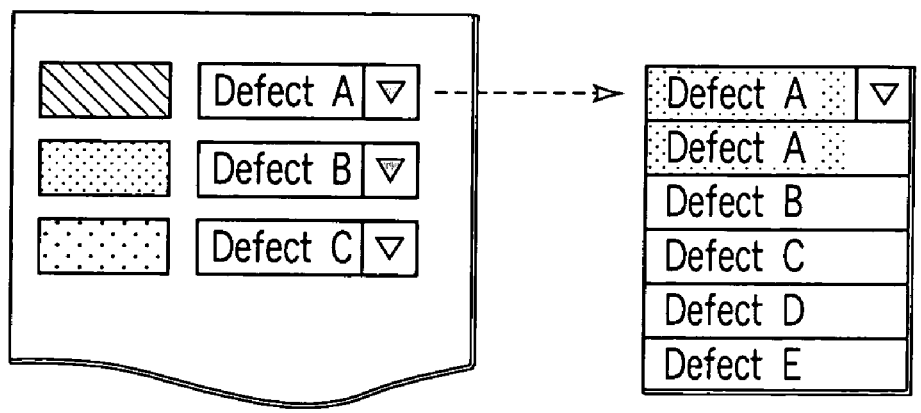
FIG. 5 is a diagram showing one example of an interface for correcting classification results.

On the other hand, when the judgment is incorrect in step S7, the user further verifies whether the result of integrating the regions is proper (step S10). Consequently, when the integration of the regions is proper, the user only corrects the judgment results using the input unit 109 (step S11). FIG. 5 shows one example of an interface for correction. After the correction, a move is made to step S8 mentioned above.

On the other hand, when the result of integrating the regions is not proper in step S10, the user selects the improper integrated regions using the input unit 109 (step S12). A method of selection can be, for example, indicating the region in the screen with a pointer.

Figure 6:
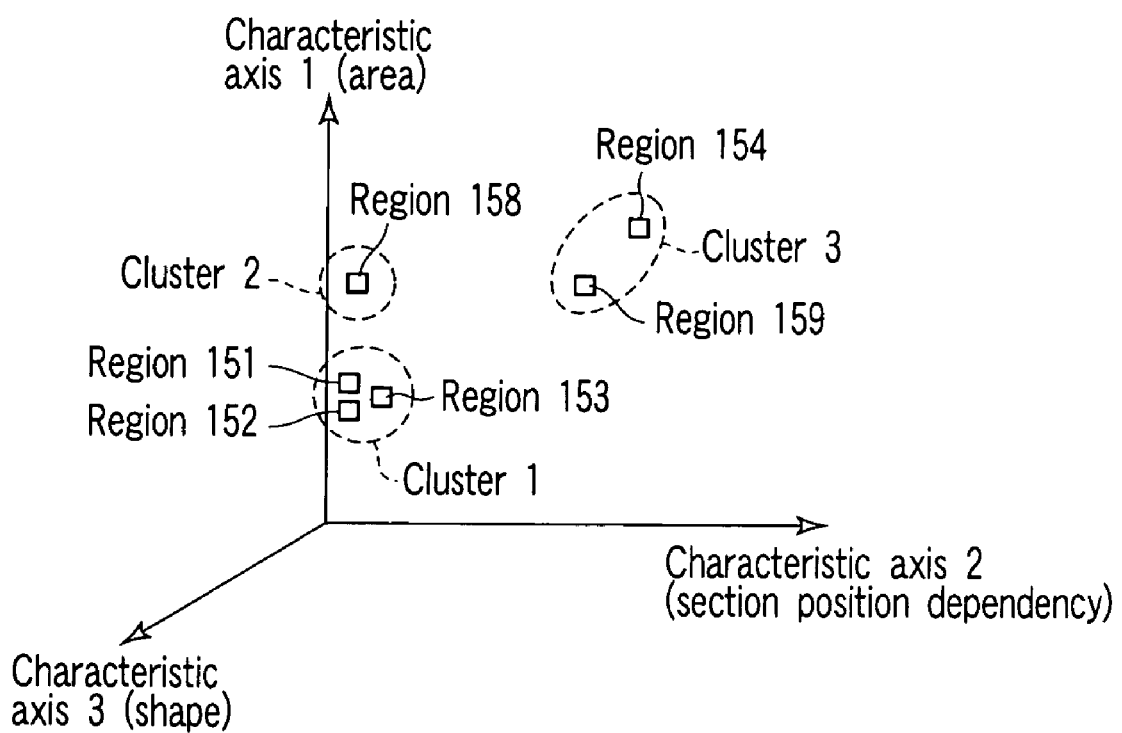
FIG. 6 is a diagram showing an example in which the respective regions in integrated regions indicated as a defect A in FIG. 3 are clustered within a characteristic space.

After the improper integrated regions are selected, the regions in the selected integrated regions are clustered within the characteristic space in the region integrating unit 104 (step S13). FIG. 6 shows an example in which the regions 151 to 154, 158 and 159 in the integrated regions indicated with slant lines in FIG. 3 are clustered within the characteristic space. Here, the regions are indicated by points corresponding to the values of their characteristic values within the characteristic space.

Figure 7:
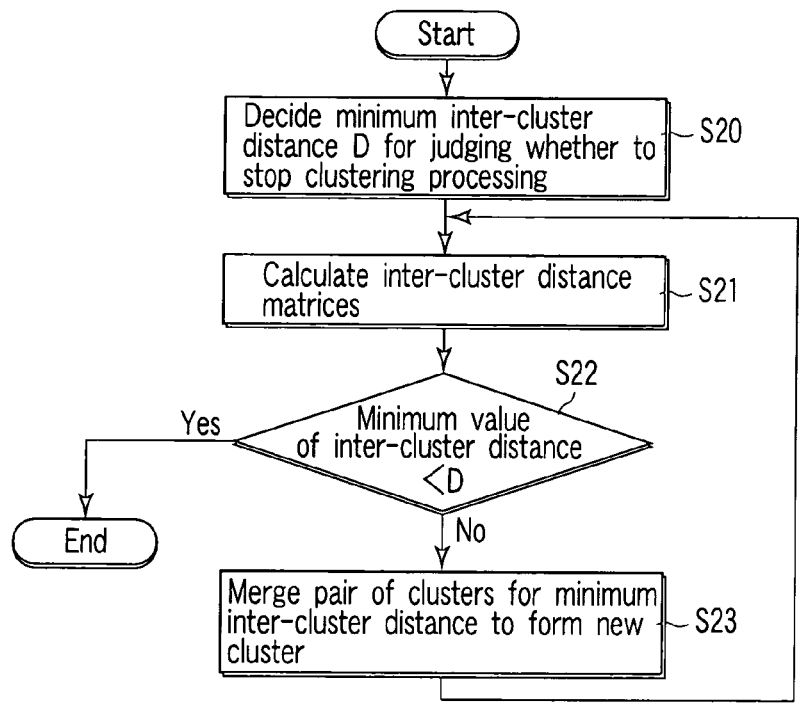
FIG. 7 is a diagram showing the flow of clustering processing by a merging method.

While there are various methods as to the technique of clustering, the flow of clustering processing by a common merging method is shown in FIG. 7 here. First, a minimum inter-cluster distance D for judging whether to stop the clustering processing is decided (step S20). Then, an inter-cluster distance matrix is calculated (step S21). Then, a judgment is made as to whether the minimum value of the inter-cluster distance is smaller than the minimum inter-cluster distance D (step S22). When the judgment results in NO, a pair of clusters for the minimum inter-cluster distance is merged to form a new cluster (step S23), and a return is made to step S21 to continue the processing. Then, when the judgment in step S22 results in YES, the processing is terminated.

It is to be noted that the minimum inter-cluster distance D for judging whether to stop the clustering processing decided in step S20 can be calculated, for example, in the following manner: an average value of inter-point distances in an initial condition (a condition where points corresponding to the regions in the integrated regions exist in the characteristic space) is multiplied by a proper coefficient; or a value of dispersion in a main component direction in the initial condition is multiplied by a proper coefficient. Moreover, the number of clusters may be used to judge whether to stop the processing. For example, the processing is continued until the number of clusters becomes two before the processing is stopped.

After the clustering processing in step S13, the regions are reintegrated for each cluster (step S14). After the reintegration, a return is made to step S6 mentioned above to continue the processing. Since the classification results of the integrated regions newly created by the reintegration are not determined yet, the judgment in step S7 results in NO, and a move is made to step S10. If the results of integration are proper in step S10, the processing is terminated after steps S11, S8 and S9 are executed.

On the other hand, when the judgment in step S10 is not proper, steps S12, S13, S14 and S6 are sequentially executed, and more detailed settings are made. However, since not all the regions are set from the beginning, labor is saved.

Figure 8:
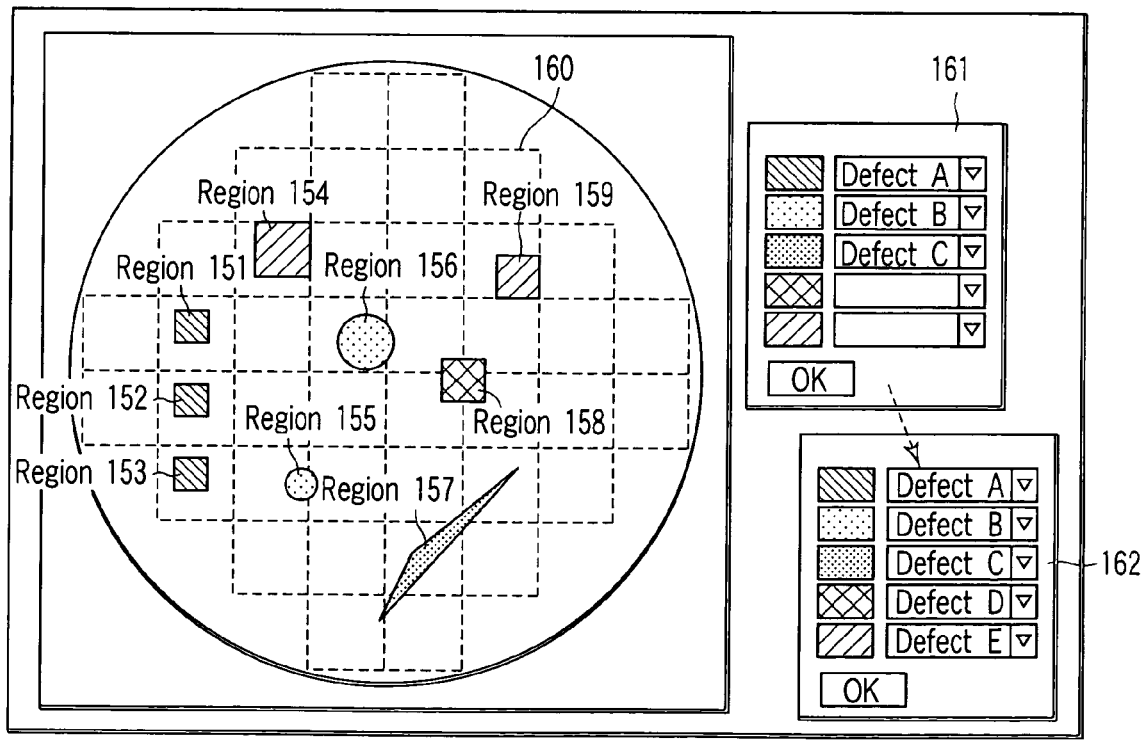
FIG. 8 is a diagram showing one example of a display screen on the display unit 108 when step S6 after step S14 is executed.

FIG. 8 shows one example of a display screen on the display unit 108 when the result of integrating the regions in the defect A in FIG. 3 is judged as improper and step S12 to S14 and S6 are thus executed. The results of reintegration based on the clustering results in FIG. 6 are displayed in a display area 160. That is, the regions "151 to 154, 158 and 159" displayed in an integrated manner as the defect A in FIG. 3 are newly displayed as three different integrated regions "151 to 153", "154 and 159" and "158" in their respective colors.

Figures 9, 10:
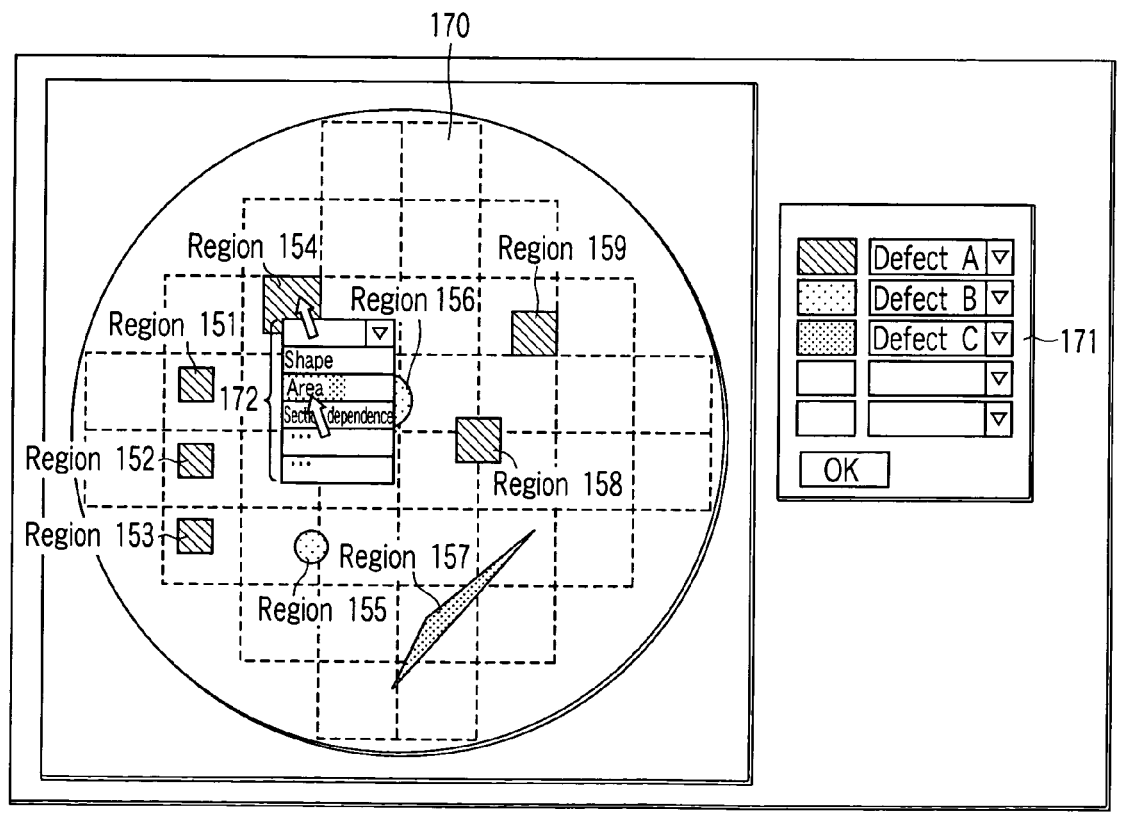
FIG. 9 is a diagram showing teacher data created on the basis of the display state shown in FIG. 8.
FIG. 10 is a diagram showing one example of a screen when the integrated regions are selected and a characteristic axis is specified.

Furthermore, an example of correction result is shown in display areas 161 and 162. The display in the display area 161 shows the contents before the correction, and the display in the display area 162 shows the contents after the correction. As indicated in the display in the display area 162, after the correction, the defect kind of the regions 151 to 153 belongs to a defect A, the defect kind of the regions 155 and 156 belongs to a defect B, the defect kind of the region 157 belongs to a defect C, the defect kind of the region 158 belongs to a defect D, and the defect kind of the regions 154 and 159 belongs to a defect E. FIG. 9 shows teacher data created on the basis of the display state shown in FIG. 8.

According to the first embodiment described above, in such a user-interactive operation as the creation of the teacher data, a plurality of regions of classification targets in an image are displayed while being automatically integrated in a suitable manner, and the teacher data is automatically created so that the contents of correction for the integrated regions are reflected in the respective regions in the integrated regions, thereby making it possible to save the trouble of correcting the individual regions and to efficiently create the teacher data.

Second Embodiment

A second embodiment of the present invention will be described below. A defect classifying apparatus in the second embodiment is characterized in that it can specify a characteristic axis used in clustering for the reintegration of regions when the improper integrated regions are selected in step S12 in FIG. 2 in the defect classifying apparatus in the first embodiment.

FIG. 10 shows one example of a screen when the integrated regions are selected and a characteristic axis is specified. As in FIG. 3, a display screen has a display area 170 for displaying each of the integrated regions in a color-coded manner and a display area 171 for displaying the defect kinds of the integrated regions. The description of regions 151 to 159 shown in FIG. 10 is similar to the description of FIG. 3 and is therefore omitted. The display area 171 is also similar to the display area 141 in FIG. 3 and is not therefore described.

Figure 11:
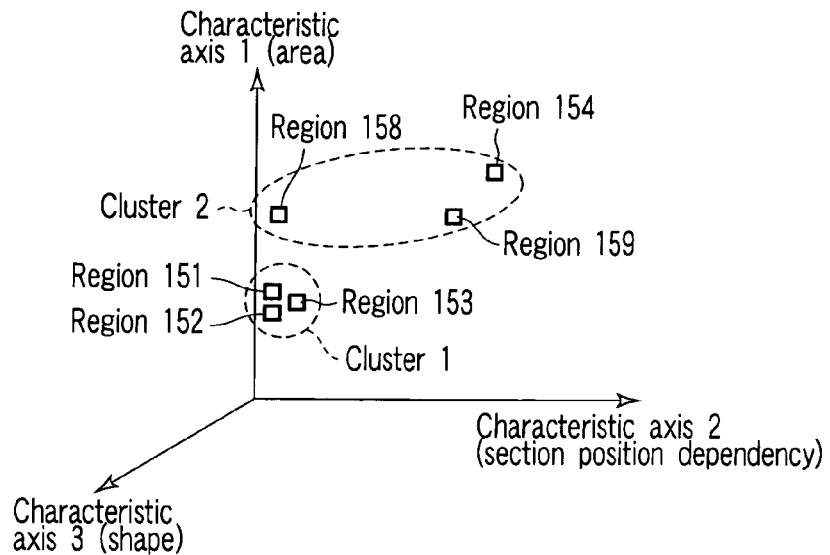
FIG. 11 is a diagram showing an example in which the regions included in the integrated regions indicated as a defect A in FIG. 10 are clustered on a characteristic axis 1 (area)
Figure 12:
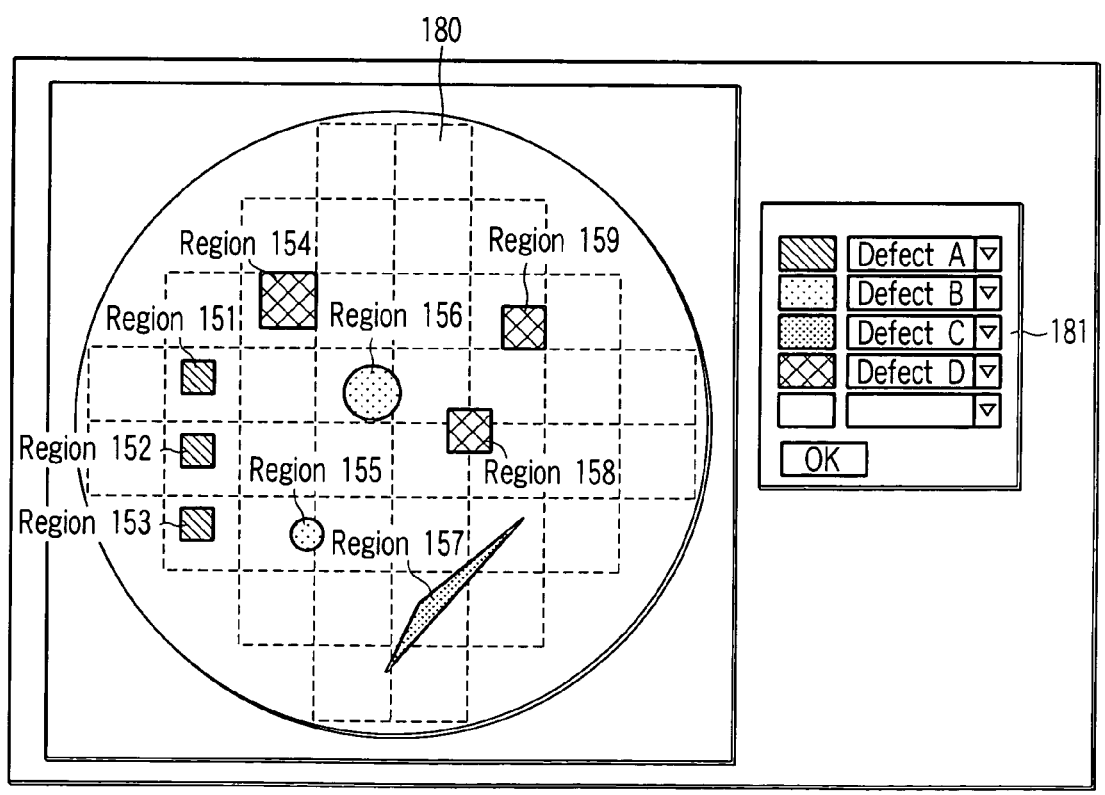
FIG. 12 is a diagram showing one example of reintegration based on the result of clustering shown in FIG. 11.

Here, the way of reintegrating the regions can be controlled by specifying the characteristic axis. For example, when the integration of the regions 151 to 154, 158 and 159 shown in FIG. 10 is incorrect and the user gives priority consideration especially to a difference depending on the area, "area" is selected from a selection menu 172 as an axis used for the clustering. Thus, since a distance is calculated along this axis indicating areal values in the clustering, the result of clustering is as shown in FIG. 11. Further, FIG. 12 shows display areas 180 and 181 displaying the result of reintegrating the defective regions on the basis of the result of this clustering.

In the display area 180, the results of the reintegration based on the result of clustering in FIG. 11 are displayed. That is, the regions "151 to 154, 158 and 159" displayed in an integrated manner as the defect A in FIG. 3 are newly displayed as two different integrated regions "151 to 153", and "154, 158 and 159" in their respective colors. Moreover, the display area 181 indicates that the defect kind of the regions 151 to 153 belongs to a defect A, the defect kind of the regions 155 and 156 belongs to a defect B, the defect kind of the region 157 belongs to a defect C, and the defect kind of the regions 154, 158 and 159 belongs to a defect D.

Figure 13:
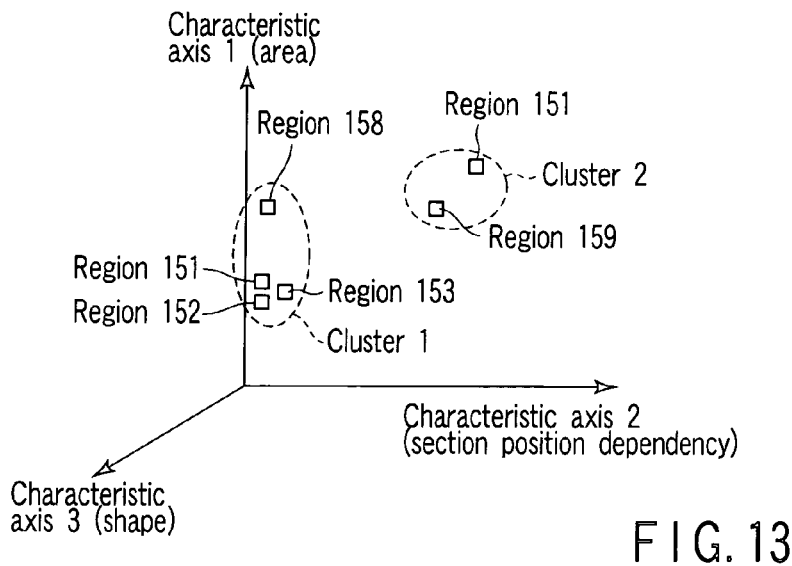
FIG. 13 is a diagram showing an example in which the regions included in the integrated regions indicated as the defect A in FIG. 10 are clustered on a characteristic axis 2.

Furthermore, when the user gives priority consideration to a difference resulting from section position dependency (there are defects dependent on the position of an exposed section of a stepper in a semiconductor wafer which is sequentially exposed to light by use of the stepper. For details, refer to Jpn. Pat. Appln. No. 2001-370218.), different clustering results as shown in FIG. 13 are obtained. Thus, the user specifies the characteristic axis to change the way of reintegration, thereby assisting the creation of the teacher data.

According to the second embodiment described above, the user specifies the reference for the reintegration of the regions such that the reintegration of the regions suited to the feeling of the user is achieved, thereby enabling the efficient creation of accurate teacher data.

Third Embodiment

Figure 14:
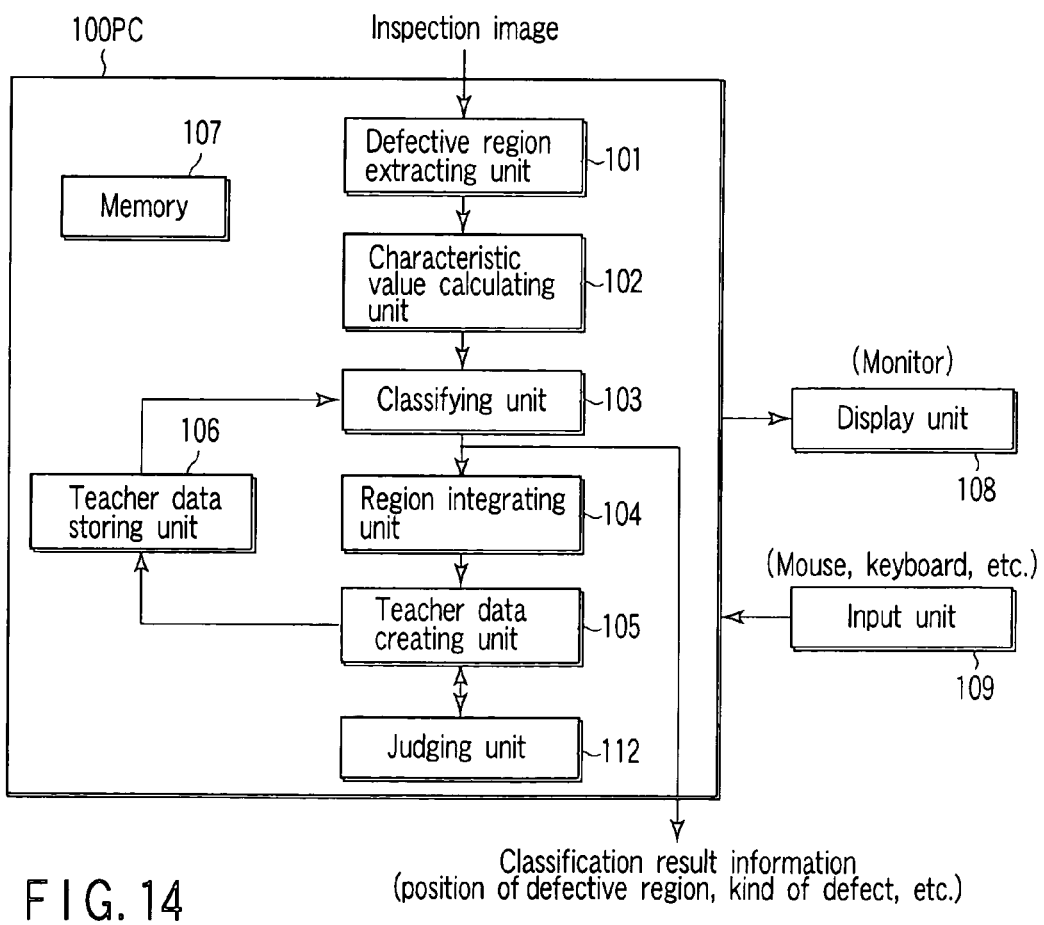
FIG. 14 is a diagram showing the configuration of a defect classifying apparatus according to a third embodiment of the present invention.

A third embodiment of the present invention will be described below. FIG. 14 shows the configuration of a defect classifying apparatus in the third embodiment. In addition to the configuration of the defect classifying apparatus in the first embodiment, the defect classifying apparatus in the third embodiment is characterized by comprising judging unit 112 for judging the necessity of creating additional teacher data from changes in the percentage of classification correctness in each class along with an increase in the number of teacher data.

When creating the teacher data, the judging unit 112 calculates the percentage of classification correctness for each defect kind on the basis of the results of an initial judgment by the classifying apparatus and the subsequent results corrected by the user. For example, when the results shown in FIG. 3 are obtained by the classifying apparatus and the results in FIG. 8 are then obtained by the correction by the user, the percentage of correctness in each defect kind is calculated in the following manner. It is to be noted that the percentage of correctness is here expressed by (the number of correct results)/(actual number).

Defect A=3/3=100%
Defect B=1/1=100%
Defect C=2/2=100%
Defect D=0/1=0%
Defect E=0/1=0%

In the process of repeating the operation of creating the teacher data, if the percentage of correctness is always calculated and changes thereof are recorded, the percentage of correctness will stably take high values for the defect kinds for which sufficient teacher data has been obtained. Thus, a certain threshold value is provided for the percentage of classification correctness. As to the defect kind in which the percentage of correctness continuously exceeding the threshold value is maintained, a judgment is made that it has sufficient teacher data. This defect kind is not displayed (or displayed in a different manner from other regions) when the results of integration are displayed. This enables the user to perform the correction operation intensively for the defect kind with a low percentage of correctness.

According to the third embodiment described above, the correction operation can be performed intensively for the regions requiring the creation of the teacher data, thereby making it possible to efficiently create the teacher data.

According to the present invention, in such a user-interactive operation as the creation of the teacher data, a plurality of regions of classification targets in an image are displayed while being automatically integrated in a suitable manner, and the teacher data is automatically created so that the contents of correction for the integrated regions are reflected in the respective regions in the integrated regions, thereby making it possible to save the trouble of correcting the individual regions and to efficiently create the teacher data for the image in which a plurality of classification targets are present.

Furthermore, according to the present invention, a user specifies the reference for the reintegration of the regions such that the reintegration of the regions suited to the feeling of the user is achieved, thereby enabling the efficient creation of accurate teacher data.

Still further, according to the present invention, a correction operation can be performed intensively for the regions requiring the creation of the teacher data, thereby making it possible to efficiently create the teacher data.

What is claimed is:

1. A learning-type classifying apparatus comprising:
   a region extracting unit for extracting a plurality of regions of classification targets from an image in which the plurality of regions of the classification targets are present;
   a characteristic value calculating unit for calculating characteristic values for the plurality of extracted regions of the classification targets;
   a classifying unit for classifying the plurality of extracted regions of the classification targets into predetermined classes based on the calculated characteristic values;
   a region integrating unit for integrating one or more of the extracted regions belonging to same classes based on the classification;
   a display unit for displaying images of the integrated regions and classification results of the classifying unit; and
   a teacher data creating unit for reflecting in each region included in the integrated regions, classification results of the integrated regions, and creating teacher data for each of the extracted regions.

2. The learning-type classifying apparatus according to claim 1, further comprising:
a judgement input unit for inputting judgement on whether the classification results of each of the integrated regions are correct or incorrect, and
wherein the region integrating unit divides an integrated region which is selected as being incorrect by the judgement input unit into a plurality of clusters based on a large/small relation of characteristic values of at least one characteristic value type, and reintegrates extracted regions belonging to each cluster of the divided integrated region.

3. The learning-type classifying apparatus according to claim 2, further comprising:
a characteristic value type input unit for inputting a characteristic value type,
wherein the region integrating unit divides the integrated region into the plurality of clusters with respect to the characteristic value type input by the characteristic value type input unit.

4. The learning-type classifying apparatus according to claim 3, further comprising a judging unit for judging a necessity of creating additional teacher data from changes in a percentage of classification correctness for each class along with an increase in a number of teacher data.

5. The learning-type classifying apparatus according to claim 2, further comprising a judging unit for judging a necessity of creating additional teacher data from changes in a percentage of classification correctness for each class along with an increase in a number of teacher data.

6. The learning-type classifying apparatus according to claim 2, wherein the region integrating unit judges whether or not to generate a new cluster by comparing an inter-cluster distance and a pre-calculated minimum inter-cluster distance.

7. The learning-type classification apparatus according to claim 2, wherein the region integrating unit divides the integrated region into the plurality of clusters based on large/small relations of characteristic values of a plurality of characteristic value types.

8. The learning-type classifying apparatus according to claim 1, further comprising a judging unit for judging a necessity of creating additional teacher data from changes in a percentage of classification correctness for each class along with an increase in a number of teacher data.

9. The learning-type classification apparatus according to claim 8, wherein when an accuracy rate of classification of an arbitrary class exceeds a predetermined value, the judging unit stops creating teacher data corresponding to that class, and the display unit one of: (i) does not display the images of the corresponding integrated region and classification results of the classification unit, and
(ii) changes a display method.

10. A learning-type classifying method for a learning-type classifying apparatus, comprising:
operating the classifying apparatus to extract a plurality of regions of classification targets from an image in which the plurality of regions of the classification targets are present;
operating the classifying apparatus to calculate characteristic values for the plurality of extracted regions;
operating the classifying apparatus to classify the plurality of extracted regions into predetermined classes based on the calculated characteristic values;
operating the classifying apparatus to integrate one or more extracted regions belonging to same classes based on the classification;
operating the classifying apparatus to display images of the integrated regions and classification results of the classification on a display unit; and
operating the classifying apparatus to reflect in each region included in the integrated regions, classification results of the integrated regions, and to create teacher data for each of the extracted regions.

11. The learning-type classifying method according to claim 10, further comprising operating the classifying apparatus to input judgement on whether the classification results of each of the integrated regions are correct or incorrect, and
wherein when a judgement that a classification result of a given integrated region is incorrect is input, said given integrated region is divided into a plurality of clusters based on a large/small relation of characteristic values of at least one characteristic value type, and extracted regions belonging to each cluster of the divided inter-grated region are reintegrated.

12. The learning-type classifying method according to claim 11, further comprising operating the classifying apparatus to input a characteristic value type, and
wherein the given integrated region is divided into the plurality of clusters with respect to the input characteristic value type.

13. The learning-type classifying method according to claim 11, further comprising operating the classifying apparatus to judge whether or not to generate a new cluster by comparing an inter-cluster distance and a pre-calculated minimum inter-cluster distance.

14. The learning-type classifying method according to claim 11, wherein said given integrated region is divided into the plurality of clusters based on large/small relations of characteristic values of a plurality of characteristic value types.

15. The learning-type classifying method according to claim 10, wherein a necessity of creating additional teacher data is judged from changes in a percentage of classification correctness for each class along with an increase in a number of teacher data.

16. The learning-type classifying method according to claim 15, wherein when an accuracy rate of classification of an arbitrary class exceeds a predetermined value:
creation of additional teacher data corresponding to that class is stopped, and
the images of the corresponding integrated region and classification results of the classification are not displayed, or a display method is changed.

* * * * *